United States Patent
Ellis

(12) 
(10) Patent No.: US 7,842,833 B2
(45) Date of Patent: Nov. 30, 2010

(54) PROCESS FOR THE PRODUCTION OF CARBONYLATION PRODUCTS

(75) Inventor: Brian Ellis, Cottingham (GB)

(73) Assignee: BP Chemicals Limited, Middlesex (GB)

( * ) Notice: Subject to any disclaimer, the term of this patent is extended or adjusted under 35 U.S.C. 154(b) by 59 days.

(21) Appl. No.: 11/791,212

(22) PCT Filed: Nov. 17, 2005

(86) PCT No.: PCT/GB2005/004452

§ 371 (c)(1),
(2), (4) Date: Mar. 18, 2008

(87) PCT Pub. No.: WO2006/061560

PCT Pub. Date: Jun. 15, 2006

(65) Prior Publication Data

US 2009/0105500 A1    Apr. 23, 2009

(30) Foreign Application Priority Data

Dec. 9, 2004    (GB) .................................. 0427021.1

(51) Int. Cl.
*C07C 67/36* (2006.01)
*C07C 51/12* (2006.01)

(52) U.S. Cl. ...................................... 560/232; 562/519
(58) Field of Classification Search ....................... None
See application file for complete search history.

(56) References Cited

U.S. PATENT DOCUMENTS

| | | | | |
|---|---|---|---|---|
| 5,218,140 A | * | 6/1993 | Wegman | 560/232 |
| 5,330,955 A | * | 7/1994 | Wegman | 502/210 |
| 5,917,089 A | * | 6/1999 | Howard | 562/519 |
| 6,387,842 B1 | * | 5/2002 | Wegman et al. | 502/300 |
| 6,521,783 B1 | | 2/2003 | Wegman et al. | |

\* cited by examiner

*Primary Examiner*—Karl J Puttlitz
(74) *Attorney, Agent, or Firm*—Nixon & Vanderhye

(57) ABSTRACT

A carbonylation process for the production of a carbonylation product such as a carboxylic acid and a carboxylic acid ester by contacting carbon monoxide with a feed comprising an alcohol such as methanol and/or a reactive derivative thereof such as methyl acetate in the vapor phase using a heterogeneous heteropolyacid catalyst which has been ion-exchanged or loaded with at least one metal selected from rhodium, iridium, copper and palladium and a Group IA metal selected from lithium, sodium, potassium and rubidium.

27 Claims, No Drawings

PROCESS FOR THE PRODUCTION OF CARBONYLATION PRODUCTS

This application is the U.S. National Phase of International Application PCT/GB2005/004452, filed 17 Nov. 2005, which designated the U.S. PCT/GB2005/004452 claims priority to British Application No. 0427021.1, filed 9Dec. 2004. The entire content of these applications are incorporated herein by reference.

The present invention relates in general to the production of a carbonylation product by the carbonylation of an alcohol and/or a reactive derivative thereof and, in particular, to the production of a carbonylation product by the vapour phase carbonylation of an alcohol and/or a reactive derivative thereof in the presence of a heterogeneous heteropolyacid carbonylation catalyst.

Acetic acid may be produced by the rhodium-catalysed, iodide-promoted carbonylation of methanol in a homogeneous liquid-phase reaction medium, such as described, for example in U.S. Pat. No. 3,769,329. The rhodium-catalysed, iodide-promoted liquid phase carbonylation of methanol is a well-known process and is operated on a commercial scale. The desirability of employing heterogeneous carbonylation catalysts for the purpose of facilitating product separation from the catalyst has also been recognised. Heterogeneous carbonylation catalysts and their use are described in a number of patent publications including, for example WO 98/57918, EP 0885870 A1 and EP 0353722 A2.

WO 98/57918 describes a process for the production of a carboxylic acid by the carbonylation of an alcohol and/or a reactive derivative thereof in the liquid phase over a heterogeneous carbonylation catalyst comprising a group VIII noble metal species on a polymeric resin having functional groups selected from nitrogen containing heterocycles. Hydrogen is added to the carbonylation to reduce leaching of the active catalytic species from the support material during carbonylation.

EP 0885870 A1 describes a process for the production of carboxylic acid and/or carboxylic acid anhydrides which comprises contacting an alcohol and//or a carboxylic acid ester, optionally water, a first hydrocarbyl halide and/or a hydrocarbyl ether reactant and a second hydrocarbyl halide promoter, with carbon monoxide in the presence of a catalyst comprising an insoluble imidazole-containing resin supporting a Group VIII metal species. The process may be performed in the liquid or the vapour phase.

EP 0353722 A2 describes a process for the vapour phase carbonylation of one or more alcohols, ethers or ether alcohols to esters and, optionally, to carboxylic acids over a solid catalyst comprising a polyoxometalate anion in which the metal is at least one taken from Group V and VI of the periodic table, such as Mo, W, V, Nb, Cr and Ta, complexed with at least one Group VIIIA cation, such as Fe, Ru, Os, Co, Rh, Ir, Ni, Pd and Pt.

U.S. Pat. No. 6,127,432 describes processes for the conversion of a feedstock comprising carbon monoxide and hydrogen to a product stream comprising at least one of an ester, acid, acid anhydride and mixtures thereof. U.S. Pat. No. 6,127,432 also describes a process for converting an alcohol, ether and/or ether alcohol to oxygentated products such as esters, acids, acid anhydrides and mixtures thereof, which process may be conducted in the vapour phase over a heterogeneous alcohol carbonylation catalyst selected from a solid superacid, clay, zeolite or molecular sieve. The alcohol carbonylation catalysts include heteropolyacids comprising a polyoxometalate anion in which a metal, or mixture of metals, selected from Groups 4, 5, 6 and 7 metals is complexed with a cation from a member of Group 7, 8, 9 10 and/or 11 metals, such as Fe, Ru, Os, Co, Rh, Ir, Ni, Pd and Pt. A preferred heteropolyacid comprises $MW_{12}PO_{40}$, wherein M is Ir, Ru, Rh, Pd and combinations thereof. U.S. Pat. No. 6,127,432 states that the stability of the heterogeneous alcohol carbonylation catalyst is improved by use of hydrogen or a feedstock containing hydrogen in the carbonylation process.

We have now found that a heterogeneous carbonylation process utilising a heteropolyacid catalyst ion-exchanged or loaded with one or more of metals selected from rhodium, iridium, copper and palladium and a Group IA promoter provides an improved carbonylation process. Reactant alcohol conversion is improved enabling the use of less catalyst to achieve a fixed amount of carbonylation product and also reduced capital and energy costs in terms of reactor construction, operation and heat management.

Accordingly, the present invention provides a carbonylation process for the production of a carbonylation product by contacting carbon monoxide with a feed comprising an alcohol and/or a reactive derivative thereof in the vapour phase using a heterogeneous heteropolyacid catalyst which has been ion-exchanged or loaded with at least one metal selected from rhodium, iridium, copper and palladium and a Group IA metal selected from the group consisting of lithium, sodium, potassium and rubidium.

Heteropolyacids are well known. Typically, the heteropolyacid anion comprises 2-18 oxygen-linked polyvalent metal atoms, which are known in the art as peripheral atoms. These peripheral atoms surround one or more central atoms in a symmetrical manner. The peripheral atoms are usually one or more of molybdenum, tungsten, vanadium, niobium, chromium and tantalum, but may be or may include other metals. The central atoms are usually silicon or phosphorus but can comprise any one of a large variety of atoms from Groups I-VIII in the Periodic Table of elements. These include, for instance, cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well known anions are named after the original researchers in this field such as, for example, the structures known as Keggin, Wells-Dawson and Anderson-Evans-Perloff structures.

Heteropolyacids may be represented by the formula $H_3M_{12}XO_{40}$ where M is tungsten, molybdenum, chromium, vanadium, tantalum or niobium and X is phosphorous or silicon.

Preferably, the heteropolyacid is selected from silicotungstic acids, silicomolybdic acids, phosphotungstic acids, phosphomolybdic acids, such as the following heteropolyacids:
12-tungstophosphoric acid $H_3[PW_{12}O_{40}].xH_2O$
12-molybdophosphoric acid $H_3[PMo_{12}O_{40}].xH_2O$
12-tungstosilicic acid $H_4[SiW_{12}O_{40}].xH_2O$
12-molybdosilicic acid $H_4[SiMo_{12})_{40}].xH_2O$ The heteropolyacids for use in the process of the present invention is a heteropolyacid which has been ion-exchanged or otherwise loaded with one or metals selected from rhodium, iridium, copper and palladium and a Group IA metal. The Group IA metal is selected from lithium, sodium, potassium and rubidium, preferably rubidium.

The total amount of metal (that is the total of the amount of rhodium, copper, iridium, and/or palladium and the amount of Group IA metal) loaded or ion-exchanged onto the heteropolyacid can vary depending on the heteropolyacid used. Suitably, however, the total amount of metal loaded onto the heteropolyacid should be such that some acidity is retained by the heteropolyacid, for example at least 0.5 protons. Thus, where 12-tungstophosphoric acid $H_3[PW_{12}O_{40}]$ is employed, up to 2.5 protons may be exchanged for metals and where 12-tungstosilicic acid $H_4[SiW_{12}O_{40}]$ is used, up to 3.5 protons can be exchanged by metals.

Before use as a catalyst, the heteropolyacid is ion-exchanged or otherwise loaded with at least one metal selected from rhodium, iridium, copper and palladium and a Group IA metal using well-known techniques. A typical example is as follows. Under nitrogen at room temperature, rhodium acetate (1 g) was dissolved in 50 ml of methanol and stirred for 1 hour. $H_3W_{12}PO_{40}$ (13 g) was added and this solution was stirred for 1 hour. To the solution was added 5.9 g silica (ex Grace grade G57) and stirred for 4 hours. The methanol was then removed by rotary evaporation under vacuum (330 mbar) for 1 hour and then under a vacuum of 100 mbar for 1 hour. The empirical formula of the composition is $Rh_x H_{3-x}W_{12}PO_{40}/SiO2$.

The heteropolyacid is preferably supported on an inert support. Suitably, the support may be selected from oxide supports such as silica, silica/aluminas, zeolites, clays, diatomaceous earths, titania and alumina. Other non-oxide supports that can be used include silicon carbide, organic polymers such as crosslinked polystyrenes and carbons. The support, such as a siliceous support, is suitably in the form of granules, beads, globules, extrudates or pellets.

Where the heteropolyacid is supported the heteropolyacid is typically present at a loading of 20-80% by weight of the total weight of the supported heteropolyacid, that is, the heteropolyacid forms 20-80% by weight of the total weight of the heteropolyacid and the support. Preferably, where the heteropolyacid is supported, the heteropolyacid is present at a loading of 30-70% by weight of the total weight of the supported heteropolyacid.

Preferably, the alcohol is an aliphatic alcohol having 1 to 12 carbon atoms, preferably 1 to 6 carbon atoms, including methanol, ethanol, propanol, isopropanol, the butanols, pentanols and hexanols. A preferred alcohol is methanol.

Reactive derivatives of the alcohol which may be used as an alternative to, or in addition to, the alcohol include one or more dialkyl ethers, esters of the alcohol and alkyl halides. Suitable reactive derivatives of methanol, for example, include methyl acetate, dimethyl ether and methyl iodide. A mixture of an alcohol and a reactive derivative thereof, for example a mixture of methanol and methyl acetate, may also be employed.

The carbonylation product is a carboxylic acid and/or the corresponding carboxylic ester. Thus, where methanol is employed as the alcohol feed, the carbonylation product comprises acetic acid and/or methyl acetate.

Water may be produced during the carbonylation process as a by-product of esterification. This water may be recycled to the reactor.

The carbon monoxide reactant may be essentially pure or may contain impurities such as carbon dioxide, methane, nitrogen, noble gases and $C_1$ to $C_4$ paraffinic hydrocarbons.

The carbon monoxide (CO) may be present in the reaction at any suitable partial pressure, such as a partial pressure of at least 0.1 bar. More particularly, the CO may be fed to the reactor in a suitable molar ratio to the alcohol feed (and/or reactive derivative), preferably at a CO to alcohol molar ratio of at least 1:1, such as at least 5:1, and/or up to 20:1, most preferably in the range 5:1 to 15:1.

The process of the invention may be operated at below atmospheric pressure, but is preferably operated at a total pressure in the range from 1 to 100 barg, preferably from 1 to 20 barg.

The process is suitably performed at a temperature in the range from 100 to 300° C., the practical upper operating temperature being dependant on the thermal stability of the catalyst. Preferably the temperature is in the range 150 to 250° C., most preferably in the range 200 to 250° C.

The process is suitably performed by contacting the reactants with the catalyst at a gas hourly space velocity (GHSV) in the range from 100 to 10000 h$^{-1}$, preferably the GHSV is in the range 500 to 5000 h$^{-1}$.

The process may be operated as a batch or continuous process, preferably as a continuous process.

The invention will now be illustrated by reference to the following examples.

EXAMPLES

Catalyst A Preparation

A rhodium substituted heteropolyacid catalyst was prepared as follows. Under nitrogen at room temperature, rhodium acetate (Aldrich, FW=221.00, 1 g) was dissolved in methanol (50 ml) with stirring for 60 minutes. After stirring of the rhodium mixture, 12-tungstophosphoric acid ($H_3[PW_{12}O_{40}]$.xH20, Aldrich, FW 2280, 13 g) was added with stirring for 1 hour. 5.9 g of silica (Grace, grade G57) was then added. The solution was then stirred for 4 hours. After 4 hours the flask was transferred to a rotary evaporator and the methanol removed under a reduced pressure of 330 mbar for 1 hour and then under a pressure of 100 mbar for a further 60 minutes. The molar ratio of Rh to heteropolyacid was 1:1 and the heteropolyacid constituted 65.4 wt % of the total weight of catalyst and support.

The empirical formula of the catalyst was $Rh_1 H_2 W_{12}O_{40}$ on silica

Catalyst 1 Preparation

Under nitrogen at room temperature, rhodium acetate (Aldrich, FW=221.00, 0.5 g) was dissolved in methanol (50 ml) with stirring for 30 minutes. After stirring of the rhodium mixture, 0.23 g of lithium acetate was added with stirring for 30 minutes. To this mixture, 12-tungstophosphoric acid ($H_3[PW_{12}O_{40}]$.xH20, Aldrich, FW 2280, 13 g) was added with stirring for 1 hour. 5.9 g of silica (Grace, grade G57) was then added. The solution was then stirred for 4 hours. After 4 hours the flask was transferred to a rotary evaporator and the methanol removed under a reduced pressure of 330 mbar for 1 hour and then under a pressure of 100 mbar for a further 60 minutes. The molar ratio of Rh to heteropolyacid was 0.5:1, the molar ratio of Rh: Li was 1:1 and the heteropolyacid constituted 67.1 wt % of the total weight of catalyst and support.

The empirical formula of the catalyst was $Rh_{0.5} Li_{0.5}H_2 W_{12}O_{40}$ on silica Catalyst 2 Preparation The procedure for Catalyst 1 was repeated except that 0.22 g of potassium acetate was used instead of lithium acetate. The empirical formula of the catalyst was $Rh_{0.5}K_{0.5}H_2 W_{12}O_{40}$ on silica Catalyst 3 Preparation The procedure for Catalyst 1 was repeated except that 0.33 g of rubidium acetate was used instead of lithium acetate. The empirical formula of the catalyst was $Rh_{0.5} Rb_{0.5}H_2 W_{12}O_{40}$ on silica Catalyst Testing Procedure 5 g of catalyst was charged to a glass reactor of diameter 1 inch with a supportive frit positioned in the middle of the tube. The reactor was then further filled with glass wool above the catalyst. The remainder of the top section of the reactor was packed with carborundum to minimise the dead volume in the reactor.

Carbon monoxide at a gas flow rate of 150 ml/min was fed into the top of the reactor for 5 minutes. The temperature was increased to 230° C. in stages of 50° C. each of 10 minutes in duration.

The system was left at temperature for 15 min to fully equilibrate and then liquid methanol was fed to the top of the reactor via a syringe pump at a rate of 1.6 ml/h.

The gas stream exiting the reactor was analysed by a gas chromatograph equipped with a Porapack QS column and a TCD detector.

The liquid products were collected in cooled glass traps and diluted with 1 g of acetonitrile solvent and analysed by liquid gas chromatograph (Carbowax 52 column).

Acetic acid and methyl acetate were products of the reaction.

The reaction conditions were 230 C, 1 atm pressure and a GHSV=1850/h. The ratio of carbon monoxide to methanol was 9. The results are given in Table 1 below.

TABLE 1

| Catalyst | Methanol conversion (%) | Time to 20% loss of conversion activity (hrs) |
|---|---|---|
| A | 26.1 | 5.1 |
| 1 | 49.7 | 7.8 |
| 2 | 27.5 | 8.0 |
| 3 | 52.6 | 9.1 |

The results of Table 1 show that the process of the present invention provides an improved conversion of methanol reactant and increased catalyst lifetime.

The invention claim is:

1. A carbonylation process for the production of a carboxylic acid and/or a carboxylic acid ester, said process comprising contacting carbon monoxide with a feed comprising an alcohol and/or a reactive derivative thereof in the vapour phase using a heterogeneous heteropolyacid catalyst which has been ion-exchanged or loaded with at least one metal selected from rhodium, iridium, copper and palladium and a Group IA metal selected from the group consisting of lithium, sodium, potassium and rubidium, wherein the heteropolyacid catalyst is represented by the formula $H_3M_{12}XO_{40}$ wherein M is tungsten, molybdenum, chromium, vanadium, tantalum or niobium and X is phosphorus or silicon.

2. A process according to claim 1 wherein the Group IA metal is selected from lithium and rubidium.

3. A process according to claim 2 wherein the Group IA metal is rubidium.

4. A process according to claim 1 wherein M is tungsten or molybdenum and X is phosphorus or silicon.

5. A process according to claim 1 wherein the heteropolyacid is selected from the group consisting of 12-tungstophosphoric acid $H_3[PW_{12}O_{40}].xH_2O$, 12-molybdophosphoric acid $H_3[PMo_{12}O_{40}].xH_2O$, 12-tungstosilicic acid $H_4[SiW_{12}O_{40}].xH_2O$, and 12-molybdosilicic acid $H_4[SiMo_{12}O_{40}].xH_2O$.

6. A process according to claim 1 wherein the total amount of metal loaded or ion-exchanged onto the heteropolyacid is such that at least 0.5 protons are retained by the heteropolyacid.

7. A process according to claim 1 wherein the heteropolyacid catalyst is supported on an inert support.

8. A process according to claim 7 wherein the support is an oxide or non-oxide support.

9. A process according to claim 7 or 8 wherein the heteropolyacid is present at a loading of 20-80% by weight based on the total weight of the heteropolyacid and the support.

10. A process according to claim 9 wherein the heteropolyacid loading is 30-70% by weight.

11. A process according to claim 1 wherein the alcohol is a $C_1$-$C_{12}$ aliphatic alcohol.

12. A process according to claim 11 wherein the alcohol is a $C_1$-$C_6$ aliphatic alcohol.

13. A process according to claim 12 wherein the alcohol is selected from methanol, ethanol, propanol, isopropanol, the butanols, pentanols and hexanols.

14. A process according to claim 13 wherein the alcohol is methanol.

15. A process according to claim 1 wherein the reactive derivative of the alcohol is selected from at least one of dialkyl ethers, esters and alkyl halides.

16. A process according to claim 1 wherein a reactive derivative of methanol is used and wherein said reactive derivative is at least one of methyl acetate, dimethyl ether and methyl iodide.

17. A process according to claim 1 wherein the feed comprises methanol and methyl acetate.

18. A process according to claim 1 wherein the gas hourly space velocity (GHSV) is in the range 100 to 10000 $h^{-1}$.

19. A process according to claim 18 wherein the GHSV is in the range 500 to 5000 $h^{-1}$.

20. A process according to claim 1 wherein the process is carried out at a pressure in the range 1 to 100 barg.

21. A process according to claim 20 wherein the pressure is in the range 1 to 20 barg.

22. A process according to claim 1 wherein the process is carried out at a temperature in the range 100 to 300° C.

23. A process according to claim 22 wherein the temperature is in the range 150 to 250° C.

24. A process according to claim 1 wherein the carboxylic acid is acetic acid and the carboxylic acid ester is methyl acetate.

25. A process according to claim 1 wherein the process is operated as a continuous or batch process.

26. A process according to claim 25 wherein the process is a continuous process.

27. A process according to claim 1 wherein the carbonylation product is acetic acid and/or methyl acetate, the feed comprises methanol and/or a methyl acetate and the catalyst is a supported tungstophosphoric heteropolyacid which has been ion-exchanged or loaded with rhodium and a Group IA metal selected from lithium and rubidium.

* * * * *